(12) United States Patent
Schultze et al.

(10) Patent No.: US 8,877,167 B2
(45) Date of Patent: Nov. 4, 2014

(54) COSMETIC COMPOSITION COMPRISING AN AQUEOUS DISPERSION OF POLYSILOXANE/POLYUREA AND A SILANE, COSMETIC TREATMENT PROCESS AND KIT THEREFOR

(75) Inventors: Xavier Schultze, Les Pavillos sous Bois (FR); Franck Hernandez, Villemomble (FR); Gregory Plos, Paris (FR); Jocelyne Dorkel, Le Plessis Bouchard (FR)

(73) Assignee: L'Oreal, Paris (FR)

( * ) Notice: Subject to any disclaimer, the term of this patent is extended or adjusted under 35 U.S.C. 154(b) by 275 days.

(21) Appl. No.: 13/146,224

(22) PCT Filed: Jan. 29, 2010

(86) PCT No.: PCT/FR2010/050149
§ 371 (c)(1),
(2), (4) Date: Nov. 30, 2011

(87) PCT Pub. No.: WO2010/086568
PCT Pub. Date: Aug. 5, 2011

(65) Prior Publication Data
US 2012/0070391 A1 Mar. 22, 2012

Related U.S. Application Data

(60) Provisional application No. 61/151,200, filed on Feb. 10, 2009.

(30) Foreign Application Priority Data

Jan. 30, 2009 (FR) ...................................... 09 50602

(51) Int. Cl.
| | |
|---|---|
| *A61Q 5/02* | (2006.01) |
| *C08G 18/61* | (2006.01) |
| *A61K 8/898* | (2006.01) |
| *A61Q 19/00* | (2006.01) |
| *A61Q 5/06* | (2006.01) |
| *C08J 3/07* | (2006.01) |
| *C08G 77/458* | (2006.01) |
| *C08L 83/10* | (2006.01) |
| *C08G 18/08* | (2006.01) |
| *C08K 5/5419* | (2006.01) |

(52) U.S. Cl.
CPC ................ *A61K 8/898* (2013.01); *C08G 18/61* (2013.01); *C08J 2383/08* (2013.01); *A61Q 19/00* (2013.01); *A61Q 5/06* (2013.01); *C08J 2375/02* (2013.01); *C08J 3/07* (2013.01); *C08G 77/458* (2013.01); *C08L 83/10* (2013.01); *C08G 18/0866* (2013.01); *C08K 5/5419* (2013.01)
USPC .................................................. 424/70.122

(58) Field of Classification Search
None
See application file for complete search history.

(56) References Cited

U.S. PATENT DOCUMENTS

| | | | | |
|---|---|---|---|---|
| 5,643,581 | A * | 7/1997 | Mougin et al. | 424/401 |
| 6,395,265 | B1 | 5/2002 | Mougin et al. | |
| 2008/0171010 | A1* | 7/2008 | Brun | 424/70.12 |
| 2008/0226576 | A1* | 9/2008 | Benabdillah et al. | 424/70.9 |
| 2009/0143496 | A1 | 6/2009 | Ziche | |
| 2009/0311211 | A1 | 12/2009 | Chrobaczek et al. | |

FOREIGN PATENT DOCUMENTS

| | | |
|---|---|---|
| DE | 103 56 494 | 7/2005 |
| DE | 10 2005 017 277 | 4/2006 |
| DE | 10 2004 058 193 | 6/2006 |
| EP | 1 672 006 | 6/2006 |
| EP | 1 935 398 | 6/2008 |

OTHER PUBLICATIONS

Pena-Alonso, R., et al., "Study of the Hydrolysis and Condensation of [Gamma]-Aminopropyltrieth Oxysilane by FT-IR Spectroscopy," Journal of Materials Science, vol. 42, No. 2, pp. 595-603, XP-019480985, (Nov. 28, 2006).
International Search Report Issued Jun. 9, 2010 in PCT/FR10/050149 filed Jan. 29, 2010.
U.S. Appl. No. 13/146,242, filed Jul. 26, 2011, Schultze, et al.

* cited by examiner

*Primary Examiner* — Brian Gulledge
(74) *Attorney, Agent, or Firm* — Oblon, Spivak, McClelland, Maier & Neustadt, L.L.P.

(57) ABSTRACT

The present invention relates to a cosmetic composition comprising an aqueous dispersion of polysiloxane/polyurea copolymer and a silane, and to a cosmetic treatment process using said composition.

19 Claims, No Drawings

COSMETIC COMPOSITION COMPRISING AN AQUEOUS DISPERSION OF POLYSILOXANE/POLYUREA AND A SILANE, COSMETIC TREATMENT PROCESS AND KIT THEREFOR

The present invention relates to cosmetic compositions comprising aqueous dispersions of silicone copolymers, which are especially nonionic and hydrogen-bond donors, mixed with a silane, and to their use in particular for cosmetically treating the hair.

The shaping of hair is generally achieved by depositing a film-forming polymer on the surface of the fiber, via the use of a styling product. It is important for this polymer to have good affinity for the fiber and good styling properties, while at the same time maintaining a pleasant cosmetic feel, especially good softness and absence of tack. This shaping nevertheless poses a few problems, especially in terms of remanence over time: specifically, the polymer may become embrittled under the constraints of styling; problems of moisture remanence: the shaping may be removed by washing with water or in the presence of surfactants; or alternatively problems of "laden" feel and of coarse and/or unnatural feel.

Moreover, compositions with a low content of volatile organic compounds (VOC) are most particularly sought.

The shaping of hair may also be performed via a chemical treatment of the fiber, such as permanent waving. In this case, the shaping of the hair has improved durability when compared with shaping by means of a styling product. However, this gain in durability is achieved by means of a chemical treatment that generally intimately modifies the hair proteins and is liable to lead to more or less substantial degradation of the physicochemical properties of the fiber, especially its intrinsic softness, hydrophilicity and/or mechanical strength.

One of the aims of the present invention is thus to propose a means for achieving long-lasting and non-degrading shaping of the fiber, especially by virtue of the combined presence of a silane and a polymer dispersion, while otherwise affording, especially by virtue of the presence of the silane, good resistance of the latex deposit (aqueous polymer dispersion), in particular shampoo resistance, which will be reflected by better resistance of the shaping of the hair.

It is also desired to obtain a natural appearance for the shaped hairstyle, and to improve the resistance of the deposit to mechanical abrasion, which will be reflected especially by the better resistance to combing (absence of appearance of particles).

The Applicants have discovered, surprisingly, that the combined use, in a cosmetic composition, of an aqueous dispersion of nonionic silicone copolymer of a silane can provide such long-lasting shaping that is non-degrading to the fiber, remanent and resistant.

It is known that the introduction of water into compositions comprising nonionic silicone polymers is difficult. Specifically, if the silicone polymer does not bear any hydrophilic grafts and/or if high concentrations of surfactants are not introduced into the formulation, precipitation of the silicone occurs, making its formulation impossible. The addition of high concentrations of surfactants is not always desirable either. In particular, in leave-in applications, the surfactant not removed may give rise to a change in the mechanical properties of the deposits, especially plasticization, or the appearance of a laden feel (greasy, transferring onto the fingers) in particular in the field of haircare.

It is known practice, in the prior art, to prepare aqueous dispersions of silicone polymers.

Thus, document U.S. 2005/137327 describes the synthesis of aqueous dispersions of polyorganosiloxane/polyurea via a process that consists in dispersing an organopolysiloxane ending with amine groups in an acidic aqueous solution preferably comprising a surfactant, in adding a diisocyanate and then in adding a base so as to regain a neutral pH and bring about polycondensation of the amino organopolysiloxane with the diisocyanate, in order finally to obtain a polyorganosiloxane/polyurea copolymer in dispersion.

However, this approach requires the handling of diisocyanates, which may pose toxicity problems. Furthermore, diisocyanates may react on contact with water and form a more or less substantial amount of diamines that are liable to intervene in the polymerization: this phenomenon may influence the polymerization, or may even harm its control and also the nature of the final dispersion obtained. Finally, the addition of acid in a first stage, and then of a base in a second stage, may be problematic for compounds that are sensitive in alkaline and acidic medium. Furthermore, this process gives rise to the formation of salts, which may harm the compositions subsequently comprising the dispersions thus prepared.

Patent FR 2 708 199 describes the synthesis of aqueous dispersions of anionic or cationic polyurethanes/polyureas. According to the described process, it is necessary to introduce a sufficiently large quantity of ionic groups to enable dispersion of the polymer in water.

Now, it has been found that an excessive content of ionic units can result in reduced water resistance of the polymer. Furthermore, there are only a limited number of anionic or cationic units that can be introduced during the synthesis, which limits the chemical diversity of the polyurethane or polyurea. Furthermore, the stability of the polymers prepared according to this process is dependent on the formulation pH, which may limit their formulation range.

In these documents, it is found that the polymer dispersion is generally prepared using monomers, which are synthesized either directly in the required solvent, or in another solvent, the synthesis then being followed in the latter case by a step of changing the solvent.

In the present invention, the aqueous dispersion of silicone copolymers is prepared from the already-formed polymer. The process used in the context of the invention allows the introduction, into the composition comprising the dispersion, of silane, a compound that is generally sparingly compatible with such an aqueous polymer dispersion. Specifically, its introduction generally brings about virtually instantaneous precipitation of the polymer in aqueous medium.

One subject of the present invention is thus a cosmetic composition comprising an aqueous dispersion of polysiloxane/polyurea copolymer derived from the reaction between at least one polymer of formula (I) as defined below and at least one diisocyanate derivative, said composition moreover comprising at least one silane of structure as defined below.

Another subject of the invention is a cosmetic treatment process, especially for making up, caring for, cleansing, coloring or shaping keratin materials, especially bodily or facial skin, the lips, the nails, the hair and/or the eyelashes, comprising the application to said materials of a cosmetic composition as defined above.

Another subject of the invention is a kit in two or more parts, comprising at least one such cosmetic composition.

It has been found that the silicone copolymer dispersions according to the invention can contain a large amount of water, which allows the easy introduction of hydrophilic compounds into the compositions. These hydrophilic compounds may prove to be advantageous in terms of affording novel cosmetic properties.

Moreover, the properties obtained with the compositions comprising these dispersions, in terms of deposition, are entirely different from those of the prior art. In particular, in the field of haircare, these compositions make it possible to obtain individualized hairs, whose coating is resistant to external mechanical stresses, such as being handled, massaged or combed.

Furthermore, the compositions according to the invention do not require the use of large amounts of solvents of VOC type, for example ethanol, or of the type such as alkanes or isododecane, for example, or alternatively of silicone type, for example D5 or D6; this allows greater latitude of formulation.

The silicone copolymers used in the context of the invention are nonionic silicones, which are hydrogen-bond donors; they are especially described in patent application U.S. 2005/ 137 327.

They may especially be derived from the reaction between:
at least one polymer of formula (I) bearing at its ends at least one reactive function containing labile hydrogen (in particular OH, SH, $NH_2$ or NHR with R=C1-C20 alkyl, C3-C40 cycloalkyl or C6-C30 aromatic); and
at least one diisocyanate-based unit.

Optionally, it is also possible to react at least one additional nonionic unit, bearing at least two reactive functions containing labile hydrogen.

The polymer of formula (I), bearing at its ends reactive units containing labile hydrogen, is of the formula:

(I)

in which:
the radicals R1, which may be identical or different, are chosen from (i) linear or branched monovalent C1-C20 hydrocarbon-based radicals, which may be unsubstituted or substituted with heteroatoms (in particular O, N, S or P) and (ii) C6-C30 aromatic radicals;
Y, which may be identical or different, represents a C1-C20 aliphatic, cycloaliphatic or aromatic hydrocarbon-based radical, comprising at least one reactive function containing labile hydrogen (especially OH, SH, $NH_2$ or NHR with R=C1-C20 alkyl, C3-C40 cycloalkyl or C6-C30 aromatic); and
n is an integer such that the average molecular weight of the polysiloxane segment is between 300 and 10 000 g/mol and preferably from 500 to 8000 g/mol.

As radicals R1 that are suitable for use in the context of the invention, mention may be made more particularly of C1-C20 alkyl radicals, and especially methyl, ethyl, propyl, isopropyl, butyl, pentyl, hexyl, octyl, decyl, dodecyl and octadecyl radicals; C3-C7 cycloalkyl radicals, in particular the cyclohexyl radical; aryl radicals, especially phenyl and naphthyl; arylalkyl radicals, especially benzyl and phenylethyl, and also tolyl and xylyl radicals.

Preferably, Y is chosen from the alkylene radicals of formula $-(CH_2)_a-$ in which a represents an integer between 1 and 10; it being understood that these radicals are substituted with at least one reactive function containing labile hydrogen, especially located at the end of the chain.

The silicones that will preferentially he chosen are these of formula:

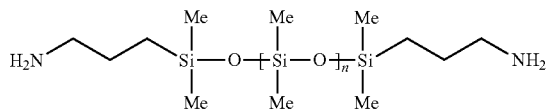

with n such that the average molecular weight (Mw) is between 300 and 10 000 g/mol.

Optionally, it is also possible to react one or more other polymers bearing reactive end groups containing labile hydrogen, chosen especially from polyethers, polyesters, polyolefins, polycarbonates, polyamides, polyimides and polypeptides. Obviously, a mixture of different polymers of formula (I) may be reacted.

The diisocyanate may be represented by the general formula (II): OCN—R—NCO, in which R is a linear, branched and/or cyclic, saturated or unsaturated, or even aromatic, C1-20 divalent alkylene group, which may be unsubstituted or substituted with one or more heteroatoms (in particular O, N, S or P).

In particular, R may be chosen from the radicals of formulae:

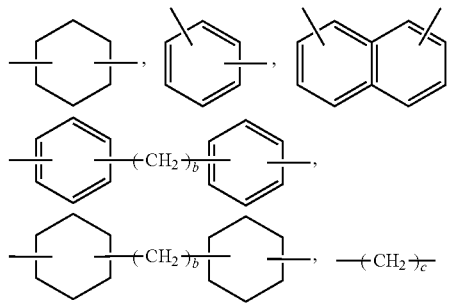

in which b is an integer between 0 and 3, and c is an integer between 1 and 20. The diisocyanate will preferentially be chosen from 1,6-hexamethylene diisocyanate, 1,4-tetramethylene diisocyanate, 4,4'-methylenedicyclohexyl diisocyanate, 4,4'-methylenediphenyl diisocyanate, 2,4-toluene diisocyanate, 2,5-toluene diisocyanate, 2,6-toluene diisocyanate, m-phenylene diisocyanate, p-phenylene diisocyanate, m-xylylene diisocyanate, tetramethyl-m-xylylene diisocyanate, naphthalene diisocyanate, butane diisocyanate, hexyl diisocyanate and isophorone diisocyanate. Needless to say, these diisocyanates may be used alone or in the form of a mixture of two or more diisocyanates.

The additional nonionic unit may be represented by formula (III): in which formula X—R'—X:
X, which may be identical or different, is a reactive function containing labile hydrogen (in particular OH, SH, $NH_2$ or NHR with R=C1-C20 alkyl, C3-C40 cycloalkyl or C6-C30 aromatic); and
R' is a linear, branched and/or cyclic, saturated or unsaturated C1-20 divalent alkylene group, which may be unsubstituted or substituted with one or more heteroatoms (in particular O, N, S or P).

Mention may be made especially of propanediol (1,2- or 1,3-), butanediol, neopentyl glycol and cyclohexanediol.

According to the invention, the copolymer is a nonionic polysiloxane/polyurea copolymer, i.e. it does not contain any ionized or ionizable groups.

Preferably, it is a block copolymer. In the context of the invention, the term "block copolymer" means a copolymer formed from at least two blocks that are different from each of the polymers constituting the copolymer in the backbone of the copolymer. For example, the copolymer of the invention contains at least one siloxane block and at least one polyurea block in the copolymer backbone.

As indicated previously, the copolymer of the invention may comprise, in addition to the polysiloxane/polyurea, other blocks of different units. Mention will be made in particular of polysiloxane/polyurea/polyurethane block terpolymers.

According to one particular embodiment, the copolymer contains a weight amount of polysiloxane of greater than 5%.

According to one particular embodiment, the amount of polysiloxane is predominant in the copolymer, preferably greater than 90% by weight relative to the total weight of the copolymer.

According to one variant, the copolymer contains solely one or more siloxane blocks and one or more polyurea blocks.

According to the invention, the copolymer may correspond to the general formula (IV):

Preferably, X represents a C2-C10 alkylene radical. Preferably, the alkylene radical X is not interrupted.

According to one particular embodiment, the group A in all the units (b) and (c), when they are present, represents NH.

According to one particularly preferred embodiment, all the groups A represent an NH radical.

Preferably, Z represents an oxygen atom or an NH radical.

Preferably, Y represents a C3-C13 hydrocarbon-based radical, which is preferably unsubstituted. Preferably, Y represents a linear or cyclic aralkylene or alkylene radical.

Preferably, D represents an alkylene radical containing at least 2 and in particular at least 4 carbon atoms, and not more than 12 carbon atoms.

Also preferably, D represents a polyoxyalkylene radical, in particular a polyoxyethylene or polyoxypropylene radical containing at least 20 and in particular at least 100 carbon atoms, and not more than 600 and in particular not more than 200 carbon atoms.

Preferably, the radical D is unsubstituted.

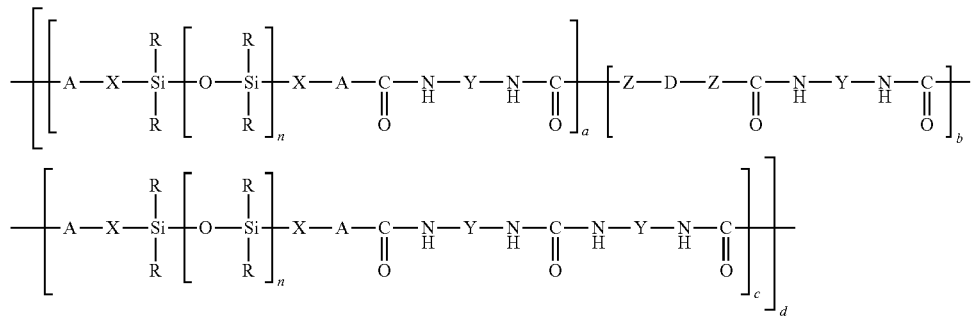

in which:
R represents a monovalent hydrocarbon-based radical, where appropriate substituted with fluorine or chlorine, containing 1 to 20 carbon atoms,
X represents an alkylene radical containing 1 to 20 carbon atoms, in which non-neighboring methylene units may be replaced with —O— radicals,
A represents an oxygen atom or an amino radical NR'—,
Z represents an oxygen atom or an amino radical NR'—,
R' represents hydrogen or an alkyl radical containing 1 to 10 carbon atoms,
Y represents a divalent hydrocarbon-based radical, where appropriate substituted with fluorine or chlorine, containing 1 to 20 carbon atoms,
D represents an alkylene radical, where appropriate substituted with fluorine, chlorine, C1-C6 alkyl or C1-C6 alkyl ester, containing from 1 to 700 carbon atoms, in which non-neighboring methylene units may be replaced with —O—, —C(O)O—, —OC(O)— or —OC(O)O— radicals,
n is a number ranging from 1 to 2000,
a is a number at least equal to 1,
b is a number ranging from 0 to 40,
c is a number ranging from 0 to 30, and
d is a number greater than 0,
on condition that A represents in at least one of the units (a) an NH radical.

Preferably, R represents a monovalent C1-C6 hydrocarbon-based radical, for example methyl, ethyl, vinyl and phenyl. According to one particular embodiment, R is an unsubstituted alkyl radical.

Preferably, n represents a number equal to at least 3 and in particular at least 25, and preferably not more than 800, in particular not more than 400 and particularly preferably not more than 250.

Preferably, a represents a number greater than 50.

When b is other than 0, b preferably represents a number not greater than 50 and in particular not greater than 25.

Preferably, c represents a number not greater than 10 and in particular not greater than 5.

The copolymers of the invention may be obtained according to the polymerization processes described in patent application U.S. 2004/0 254 325 or patent application WO 03/014 194.

The copolymer may thus be obtained via a two-step process, such that:
in the first step, a silazane of formula (2) or (2'):

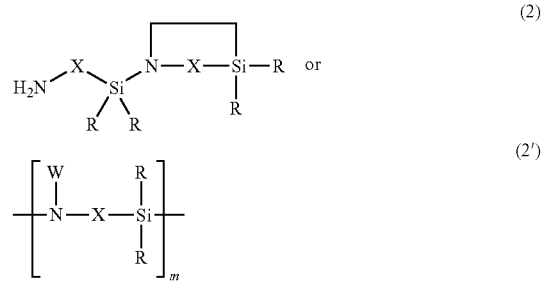

W representing a hydrogen atom, a substituted or unsubstituted hydrocarbon-based radical, preferably containing from 1 to 20 carbon atoms, or a radical $R_2Si\text{—}X\text{—}NH_2$;

is reacted with an organosilicon compound of general formula (3):

$$(HO)(R_2SiO)_{n-1}[H] \qquad (3)$$

to obtain an aminoalkylpolydiorganosiloxane of general formula (4):

$$H_2N\text{—}X\text{—}[SiR_2O]_nSiR_2\text{—}X\text{—}NH_2 \qquad (4)$$

in a second step, the aminoalkylpolydiorganosiloxane of general formula (4) is polymerized with a diisocyanate of general formula (5):

$$OCN\text{—}Y\text{—}NCO \qquad (5)$$

In general, in the first step, silazanes of general formula (2) or (2') and reagents containing silanol groups are used in equimolar proportions.

For the preparation of very pure silicones containing bisaminoalkyl end groups, of general formula (4), a small excess of the silazane compound of general formula (2) or (2'), which may then be removed, in an additional simple process step, for instance the addition of small amounts of water, is preferably used.

If b is at least 1, up to 95% by weight, on the basis of all of the components used, of chain extenders, which are chosen from diamines, hydroxy compounds blocked with an isocyanate, dihydroxy compounds or mixtures thereof, may be used during the second step.

Preferably, the chain extenders have the general formula (6): HZ-D-ZH (6) in which D and Z have the preceding meanings. If Z has the meaning O, the chain extender of general formula (6) may also be reacted before the reaction in the second step, with the diisocyanate of general formula (5). Where appropriate, water may be used as chain extender.

Examples of diisocyanates of general formula (5) to be used are aliphatic compounds such as isophorone diisocyanate, 1,6-hexamethylene diisocyanate, 1,4-tetramethylene diisocyanate and 4,4'-methylene-dicyclohexyl diisocyanate or aromatic compounds, for instance 4,4'-methylenediphenyl diisocyanate, 2,4-toluene diisocyanate, 2,5-toluene diisocyanate, 2,6-toluene diisocyanate, m-phenylene diisocyanate, p-phenylene diisocyanate, m-xylylene diisocyanate, tetramethyl-m-xylylene diisocyanate, or mixtures of these isocyanates. An example of a commercially available compound is a diisocyanate of the Desmodur® series (H, I, M, T or W) from Bayer A G, Germany. Aliphatic diisocyanates, in which Y is an alkylene radical, are preferred since they lead to materials that have improved UV stabilities.

The alkylenes containing $\alpha,\omega$-OH end groups of general formula (6) are preferably polyalkylenes or polyoxyalkylenes. They are preferably essentially free of contaminations of mono- or trifunctional polyoxyalkylenes or polyoxyalkylenes of higher functionality. Polyetherpolyols, polytetramethylenediols, polyesterpolyols or polycaprolactonediols, but also polyalkylenes containing $\alpha,\omega$-OH end groups based on poly(vinyl acetate), poly(vinyl acetate)-ethylene copolymers, poly(vinyl chloride) copolymers or polyisobutyldiols may be used here. Preferably, polyoxyalkyls and particularly preferably polypropylene glycols are used. Such compounds are commercially available as base materials, inter alia, for polyurethane foams and for uses as coatings, with molecular masses Mn of up to 10 000. Examples are the polyether polyols and polyester polyols Baycoll® from Bayer A G, Germany, or the polyether polyols Acclaim® from Lyondell Inc., USA. $\alpha,\omega$-Alkylenediol monomers, for instance ethylene glycol, propanediol, butanediol or hexanediol, may also be used. Moreover, for the purposes of the invention, the term "dihydroxylated compounds" also means bishydroxyalkyl silicones, such as those sold, for example, by the company Goldschmidt under the names Tegomer H—Si 2111, 2311 and 2711.

The preparation of the copolymers described above of general formula (I) may be performed in solution, but also in solid form, in continuous or batch mode.

If the amount of urethane or urea segments is large, a solvent having a high solubility parameter is chosen, for instance dimethylacetamide. THF may also be used. According to one particular embodiment, the synthesis of the copolymer is performed without solvent.

The synthesis is preferably performed in the absence of moisture and under a protective gas, usually nitrogen or argon.

The reaction is preferably performed in the presence of a catalyst. The catalysts that are suitable for the preparation are dialkyltin compounds, for instance dibutyltin dilaurate or dibutyltin diacetate, or tertiary amines, for instance N,N-dimethylcyclohexanamine, 2-dimethylaminoethanol or 4-dimethylaminopyridine. According to one particular embodiment, the copolymer that is useful in the present invention does not contain any polyurethane.

Examples of copolymers that may be mentioned include the dimethylpolysiloxane/urea copolymer, of INCI name polyureadimethicone.

Mention may be made especially of commercial polymers such as Belsil UD-60 (Wacker SLM TPSE 60 or Geniomer 60), Belsil UD-80 (Wacker SLM TPSE 80 or Geniomer 80), Wacker Belsil UD-140 (Wacker SLM TPSE 180 or Geniomer 180, and Wacker Belsil UD-200 (Wacker SLM TPSE 200 or Geniomer 200) sold by the company Wacker.

Preferably, the copolymers according to the invention have a number-average molecular mass (Mn) of between 1000 and 5 000 000, especially between 2000 and 1 000 000 and more preferentially between 2000 and 100 000 g/mol.

The use of these copolymers as an aqueous dispersion, in the presence of silane, may require a dispersion process, which preferably comprises the following steps:
  dissolution of the copolymer in an organic phase composed of one or more cosmetic oils and/or solvents;
  addition of said organic phase comprising the polymer to an aqueous phase comprising one or more surfactants, followed by emulsification with rapid stirring. Optionally, all or some of the cosmetic oils or solvents used to dissolve the polymer may be evaporated off via any technique considered appropriate by a person skilled in the art, such as evaporation under vacuum.

An aqueous dispersion of silicone copolymer that is stable over time (absence of macroscopic phase separation after 5 days at room temperature) may thus be obtained.

As cosmetic oil or solvent that may be used in the context of the invention, mention may be made of any liquid compound (at 20-25° C., 1 atm.) that is insoluble in water and solubilizing for the copolymer.

The term "insoluble in water" refers to a compound whose solubility in water (at 25° C., 1 atm.) is less than 1% by weight.

The term "solubilizing for the copolymer" refers to a compound that enables the dissolution of at least 1% by weight of polymer (at 25° C., 1 atm.).

Preferably, at least one solvent compound with a boiling point of less than 150° C., at 1 atm., and/or a solvent compound that can form an azeotrope with water, is used.

Mention may be made especially of the following compounds, it being understood that they are liquid at 20-25° C., 1 atm.:
- linear or branched, saturated or unsaturated, optionally cyclic or aromatic C5-C30 alcohols or polyols, which may contain heteroatoms (O, N, P or S); and more particularly saturated, linear or branched C5-C30 alcohols or polyols; or even saturated, linear or branched C5-C20 alcohols or polyols; preferentially monoalcohols;
- esters of monoalcohols or polyols and of monoacids or polyacids, and in particular triglycerides such as plant oils and esters of general formula R3—O—CO—R4, in which R3 and R4, which may be identical or different, are linear or branched, or even cyclic, saturated or unsaturated, preferably C3-C30 or even C4-C20 alkyl hydrocarbon-based radicals; in particular, R3 is preferably a C1-C6 or even C2-C4 alkyl; in particular, R4 is preferably a C1-C18 or even C1-C15 alkyl;
- ketones of the type R3—CO—R4 in which R3 and R4, which may be identical or different, are linear or branched, or even cyclic, saturated or unsaturated, preferably C3-C30 alkyl hydrocarbon-based radicals; preferentially, R3 and R4 are linear or branched C4-C8 alkyls;
- aromatic hydrocarbons, such as toluene;
- linear, cyclic or branched C5-C30 alkanes; preferably C6-C20, better still C10-C16, or even C11-C13;
- volatile or nonvolatile silicone oils; mention may be made especially of polydimethylsiloxanes (PDMS), phenylated polyorganosiloxanes such as phenyl trimethicones, phenyltrimethylsiloxydiphenylsiloxanes, diphenylmethyldimethyltrisiloxanes, diphenyl dimethicones, phenyl dimethicones and polymethylphenylsiloxanes, which are optionally fluorinated; polysiloxanes modified with fatty acids, fatty alcohols or polyoxyalkylenes, fluoro silicones and perfluoro silicone oils.

Among the preferred silicone oils, mention may be made of polydimethylsiloxanes, polymethylphenylsiloxanes, silicones comprising polyoxyalkylene blocks or grafts, in particular polyoxyethylene or copoly(oxyethylene/oxypropylene) such as dimethicone copolyols, silicones bearing both hydrocarbon-based hydrophobic groups (for example $C_2$-$C_{30}$ alkyl groups) and polyoxyethylene or copoly(oxyethylene/oxypropylene) blocks or grafts such as alkyldimethicone copolyols, silicones bearing fluoro or perfluoro groups, such as perfluoroalkyl polydimethylsiloxanes and perfluoroalkyl polymethylphenylsiloxanes, and mixtures thereof. These silicone oils may optionally comprise alkyl or alkoxy groups that are pendent or at the end of a silicone chain.

Mention may also be made of linear or cyclic silicones, in particular comprising from 2 to 7 silicon atoms. Mention may be made especially of octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Among these solvents, ethyl acetate, butyl acetate, propyl acetate, isopropyl acetate, isopropyl palmitate, pentanol, hexanol, heptanol, heptane, decane, dodecane, isododecane, undecane, tridecane, cyclotetramethylsiloxane (D4), cyclopentamethylsiloxane (D5), cyclohexamethylsiloxane (D6), methyl ethyl ketone and toluene;
and also mixtures thereof, will preferentially be chosen.

Needless to say, a mixture of solvents may be employed.

In one particular embodiment, a solvent of linear or branched C5-C20 alcohol type is used, alone or as a mixture with a C5-C20 alkane, a cyclic volatile silicone oil and/or a C4-C20 ester, which are themselves alone or as a mixture.

The surfactants that may be used may be anionic, cationic, amphoteric or nonionic; a mixture of surfactants may be used.

Preferably, the surfactants are cationic or anionic, preferentially cationic.

The following anionic surfactants, which may be used alone or as mixtures, may be mentioned: mention may be made especially of the salts, in particular the alkali metal salts such as the sodium salts, the ammonium salts, the amine salts, the amino alcohol salts or the salts of alkaline-earth metals, for example of magnesium, of the following compounds: alkyl sulfates, alkyl ether sulfates, alkylamido ether sulfates, alkylaryl polyether sulfates, monoglyceride sulfates; alkylsulfonates, alkyl phosphates, alkylamidesulfonates, alkylarylsulfonates, α-olefin sulfonates, paraffin sulfonates; alkyl sulfosuccinates, alkyl ether sulfosuccinates, alkylamide sulfosuccinates; alkyl sulfoacetates; acylsarcosinates; and acylglutamates, the alkyl or acyl groups of all these compounds comprising from 6 to 24 carbon atoms and the aryl group preferably denoting a phenyl or benzyl group. It is also possible to use esters of $C_6$-$C_{24}$ alkyl and of polyglycosidecarboxylic acids, such as alkyl glucoside citrates, polyalkyl glycoside tartrates and polyalkyl glycoside sulfosuccinates; alkyl sulfosuccinamates, acyl isethionates and N-acyltaurates, the alkyl or acyl group of all these compounds containing from 12 to 20 carbon atoms. Among the anionic surfactants that may also be used, mention may also be made of acyl lactylates in which the acyl group contains from 8 to 20 carbon atoms. Mention may also be made of alkyl-D-galactosideuronic acids and salts thereof, and also polyoxyalkylenated ($C_6$-$C_{24}$)alkylether-carboxylic acids, polyoxyalkylenated ($C_6$-$C_{24}$)alkyl($C_6$-$C_{24}$)arylethercarboxylic acids and polyoxyalkylenated ($C_6$-$C_{24}$)alkylamidoethercarboxylic acids and salts thereof, in particular those comprising from 2 to 50 ethylene oxide groups, and mixtures thereof.

Among the preferred anionic surfactants, mention may be made of the salts, in particular of sodium, of magnesium or of ammonium, of alkyl sulfates; of alkyl ether sulfates, for instance sodium lauryl ether sulfate, preferably containing 2 or 3 mol of ethylene oxide; of alkyl ether carboxylates; and mixtures thereof, the alkyl groups generally containing from 6 to 24 carbon atoms and preferably from 8 to 16 carbon atoms.

As nonionic surfactants that may be used in the context of the invention, mention may be made of polyethoxylated, polypropoxylated or polyglycerolated alcohols, alpha-diols, ($C_1$-$C_{20}$)alkylphenols and fatty acids, containing a fatty chain comprising, for example, from 8 to 18 carbon atoms, ethylene oxide or propylene oxide groups possibly ranging especially from 2 to 50, and the number of glycerol groups possibly ranging especially from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines, preferably having from 2 to 30 mol of ethylene oxide; ethoxylated fatty acid esters of sorbitan having from 2 to 30 mol of ethylene oxide; fatty acid esters of sucrose, fatty acid esters of polyethylene glycol, ($C_6$-$C_{24}$)alkylpolyglycosides, N-($C_6$-$C_{24}$) alkylglucamine derivatives, amine oxides such as ($C_{10}$-$C_{14}$) alkylamine oxides or N-($C_{10}$-$C_{14}$) acylaminopropylmorpholine oxides; and mixtures thereof.

Among the amphoteric surfactants, mention may be made of aliphatic secondary or tertiary amine derivatives, in which the aliphatic group is a linear or branched chain containing 8 to 22 carbon atoms and containing at least one water-soluble anionic group, such as, for example, a carboxylate, sulfonate, sulfate, phosphate or phosphonate group; mention may also be made of ($C_8$-$C_{20}$)alkylbetaines, sulfobetaines, ($C_8$-$C_{20}$)alkyl-amido-($C_6$-$C_8$)-alkyl-betaines or ($C_8$-$C_{20}$)alkyl-amido-($C_6$-$C_8$)-alkylsulfobetaines; and mixtures thereof.

Among the amine derivatives that may be mentioned are the products sold under the name Miranol®, as described in patents U.S. Pat. Nos. 2,528,378 and 2,781,354 and classified in the CTFA dictionary, 3rd edition, 1982, under the names Amphocarboxyglycinate and amphocarboxypropionate, having the respective structures (2) and (3):

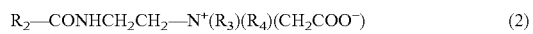
$$R_2—CONHCH_2CH_2—N^+(R_3)(R_4)(CH_2COO^-) \quad (2)$$

in which:
$R_2$ represents an alkyl group derived from an acid $R_2$—COOH present in hydrolyzed coconut oil, or a heptyl, nonyl or undecyl group,
$R_3$ represents a beta-hydroxyethyl group, and
$R_4$ represents a carboxymethyl group;
and

$$R_{2'}—CONHCH_2CH_2—N(B)(C) \quad (3)$$

in which:
B represents —$CH_2CH_2OX'$,
C represents —$(CH_2)_z$-Y', with z=1 or 2,
X' represents the —$CH_2CH_2$—COOH group or a hydrogen atom,
Y' represents —COON or the —$CH_2$—CHOH—$SO_3H$ group,
$R_{2'}$ represents an alkyl group of an acid $R_{9'}$—COOH present in coconut oil or in hydrolyzed linseed oil, an alkyl group, especially a $C_{17}$ group and its iso form, or an unsaturated $C_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid and cocoamphodipropionic acid.

By way of example, mention may be made of the cocoamphodiacetate sold under the trade name Miranol® C2M Concentrate by the company Rhodia.

Among the amphoteric surfactants that are preferably used are ($C_8$-$C_{20}$)alkylbetaines, ($C_8$-$C_{20}$)alkylamido($C_6$-$C_8$)alkylbetaines and alkylamphodiacetates, and mixtures thereof.

Among the cationic surfactants, mention may be made of:
i) alkylpyridinium salts, ammonium salts of imidazoline, diquaternary ammonium salts, and ammonium salts containing at least one ester function;
ii) quaternary ammonium salts having the following general formula:

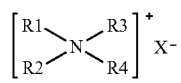

in which the radicals R1 to R4, which may be identical or different, represent a linear or branched aliphatic radical containing from 1 to 30 carbon atoms, or an aromatic radical such as aryl or alkylaryl; the aliphatic radicals may optionally comprise heteroatoms (O, N, S or halogens).

The aliphatic radicals are chosen, for example, from C12-C22 alkyl, alkoxy, C2-C6 polyoxyalkylene, alkylamide, (C12-C22)alkylamido(C2-C6)alkyl, (C12-C22)alkyl-acetate and hydroxyalkyl radicals, containing from 1 to 30 carbon atoms. $X^-$ is an anion chosen from the group of halides, phosphates, acetates, lactates, C2-C6 alkyl sulfates and alkyl or alkylarylsulfonates.

iii) quaternary ammonium salts of imidazoline of formula:

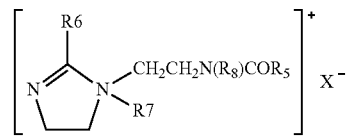

in which:
R5 represents an alkenyl or alkyl radical containing from 8 to 30 carbon atoms, for example fatty acid derivatives of tallow or of coconut,
R6 represents a hydrogen atom, a C1-C4 alkyl radical or an alkenyl or alkyl radical containing from 8 to 30 carbon atoms,
R7 represents a C1-C4 alkyl radical,
R8 represents a hydrogen atom or a C1-C4 alkyl radical,
X' is an anion chosen from the group of halides, phosphates, acetates, lactates, C2-C6 alkyl sulfates, alkylsulfonates or alkylarylsulfonates.

R5 and R6 preferably denote a mixture of alkenyl or alkyl radicals containing from 12 to 21 carbon atoms, such as, for example, fatty acid derivatives of tallow, R7 denotes methyl and R8 denotes hydrogen. Such a product is, for example, Quaternium-27 (CTFA 1997) or Quaternium-83 (CTFA 1997), which are sold under the names Rewoquat® W75, W90, W75PG and W75HPG by the company Witco, iv) diquaternary ammonium salts of formula:

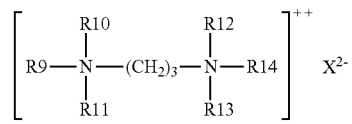

in which:
R9 denotes an aliphatic radical containing from about 16 to 30 carbon atoms,
R10, R11, R12, R13 and R14, which may be identical or different, are chosen from hydrogen and an alkyl radical containing from 1 to 4 carbon atoms, and
$X^-$ is an anion chosen from the group of halides, acetates, phosphates, nitrates, ethyl sulfates and methyl sulfates.

Such diquaternary ammonium salts in particular comprise propanetallowdiammonium dichloride;

v) quaternary ammonium salts containing at least one ester function, such as those of formula:

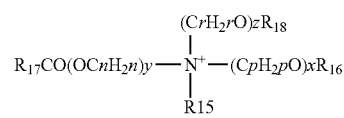

in which:
R15 is chosen from C1-C6 alkyl radicals and C1-C6 hydroxyalkyl or dihydroxyalkyl radicals;
R16 is chosen from the radical R19—CO—, linear or branched, saturated or unsaturated C1-C22 hydrocarbon-based radicals R20, a hydrogen atom;

R18 is chosen from the radical R21—CO, linear or branched, saturated or unsaturated C1-C22 hydrocarbon-based radicals R22, a hydrogen atom;

R17, R19 and R21, which may be identical or different, are chosen from linear or branched, saturated or unsaturated C7-C21 hydrocarbon-based radicals;

r, n and p, which may be identical or different, are integers ranging from 2 to 6;

y is an integer ranging from 1 to 10;

x and z, which may be identical or different, are integers ranging from 0 to 10;

$X^-$ is a simple or complex organic or mineral anion;

with the proviso that the sum x+y+z is from 1 to 15, that when x is 0, then R16 denotes R20 and that when z is 0, then R18 denotes R22.

The alkyl radicals R15 may be linear or branched, and more particularly linear. Preferably, R15 denotes a methyl, ethyl, hydroxyethyl or dihydroxypropyl radical, and more particularly a methyl or ethyl radical.

Advantageously, the sum x+y+z is from 1 to 10.

When R16 is a hydrocarbon-based radical R20, it may contain from 12 to 22 carbon atoms, or contain from 1 to 3 carbon atoms.

When R18 is a hydrocarbon-based radical R22, it preferably contains 1 to 3 carbon atoms.

Advantageously, R17, R19 and R21, which may be identical or different, are chosen from linear or branched, saturated or unsaturated C11-C21 hydrocarbon-based radicals, and more particularly from linear or branched, saturated or unsaturated C11-C21 alkyl and alkenyl radicals.

Preferably, x and z, which may be identical or different, are equal to 0 or 1. Advantageously, y is equal to 1.

Preferably, r, n and p, which may be identical or different, are equal to 2 or 3 and even more particularly equal to 2.

The anion $X^-$ is preferably a halide (chloride, bromide or iodide) or a C1-C4 alkyl sulfate, more particularly methyl sulfate. The anion $X^-$ may also represent methanesulfonate, phosphate, nitrate, tosylate, an anion derived from an organic acid (such as acetate or lactate), or any other anion that is compatible with the ammonium containing an ester function.

The surfactants may be, for example, the salts (chloride or methyl sulfate) of diacyloxyethyldimethylammonium, of diacyloxyethylhydroxyethyldimethylammonium, of monoacyloxyethylhydroxyethyldimethylammonium, of triacyloxyethylmethylammonium, of monoacyloxyethylhydroxyethyldimethylammonium, and mixtures thereof. The acyl radicals preferably contain 14 to 18 carbon atoms and are more particularly derived from a plant oil, for instance palm oil or sunflower oil. When the compound contains several acyl radicals, these radicals may be identical or different. Such compounds are sold, for example, under the names Dehyquart® by the company Cognis, Stepanquat® by the company Stepan, Noxamium® by the company Ceca, and Rewoquat®WE 18 by the company Rewo-Goldschmidt.

vi) quaternary ammonium salts and in particular behenyltrimethylammonium chloride, dipalmitoylethylhydroxyethylmethylammonium methosulfate, cetyltrimethylammonium chloride, quaternium-83, behenylamidopropyl-2,3-dihydroxypropyldimethylammonium chloride and palmitylamidopropyltrimethylammonium chloride.

Other ingredients may be present in the aqueous dispersion of silicone copolymer according to the invention; these ingredients may be introduced, for example, into the aqueous phase or the organic phase, during the preparation of the dispersion. Mention may thus be made, alone or as a mixture, of: cationic, anionic and/or non-ionic silicones bearing hydrophilic or hydrophobic grafts; plasticizers; spreading agents or coalescers; solid fatty substances such as fatty alcohols, fatty acids or plant or mineral waxes; conditioning agents, especially of cationic polymer type including polyamines; anionic (neutralized or non-neutralized), cationic or nonionic polymers and especially styling polymers; pH agents, bases or acids; organic or mineral pigments or colorants; sunscreens, fragrances, peptizers, preserving agents, amino acids or vitamins; thickeners; silanes.

As has been mentioned hereinabove, a process for preparing the aqueous dispersions of polysiloxane/polyurea according to the invention comprises the following steps:

i) dissolving the copolymer in an organic phase;

Preferably, the copolymer is present in a proportion of from 2% to 60% by weight, especially 5% to 40% by weight or even 8% to 25% by weight, in the organic phase.

ii) preparing an aqueous phase comprising one or more surfactants;

Preferably, the surfactant(s) are present in a proportion of from 0.01% to 15% by weight, especially 0.05% to 10% by weight or even 0.1% to 6% by weight, in the aqueous phase.

iii) mixing together the organic and aqueous phases, and then emulsifying, especially with rapid stirring.

Preferably, the surfactant represents 0.01% to 15% by weight, especially 0.05% to 10% by weight or even 0.1% to 5% by weight relative to the weight of the organic phase comprising the copolymer.

Preferably, 0.5 to 50 parts by weight and in particular 0.8 to 20 parts of aqueous phase comprising the surfactants are added, especially 1 to 12 parts, or even 2 to 8 parts, per 1 part of organic phase comprising the copolymer.

Preferably, the emulsification is performed at a temperature from 15 to 100° C., especially 18 to 50° C., or even 20-30° C., at a speed of between 50 and 30 000 rpm and especially 200 to 10 000 rpm, via any means known to those skilled in the art, especially with a homogenizer, in particular of the Ultra-Turrax type.

Optionally, all or part of the organic phase may then be evaporated, via any technique considered adequate by a person skilled in the art, such as evaporation under reduced pressure (under vacuum).

It is thus possible finally to obtain an aqueous dispersion of polysiloxane/polyurea copolymer, whose solids content may be between 0.1% and 50% by weight, especially 0.5% to 40% by weight, or even 1% to 30% by weight and better still 2% to 25% by weight.

The dispersion according to the invention may comprise solvent compounds and/or an organic phase, which may represent 0.05% to 80% by weight and especially 1% to 70% by weight of said dispersion. This organic phase may also be absent (less than 0.05%, or even 0%).

The dispersion may also comprise surfactants, which may represent 0.05% to 10% by weight, especially 0.01% to 8% by weight or even 0.1% to 5% by weight of said dispersion. These surfactants may also be absent (less than 0.05%, or even 0%).

The amount of polymer present in the compositions according to the invention obviously depends on the type of composition and on the desired properties; it may range between 0.01% and 30% by weight, preferably between 0.1% and 20% by weight, especially between 0.5% and 10% by weight, or even between 1% and 5% by weight of polymer solids relative to the weight of the cosmetic composition.

The cosmetic composition according to the invention moreover comprises at least one silane of structure:

in which:
X represents a C1-C6 alkoxy group, more particularly ethoxy;
Y represents a C1-C6 alkoxy group, more particularly ethoxy; or C1-C6 alkyl, more particularly methyl;
Z is a linear or branched, saturated or unsaturated C1-C22 hydrocarbon-based chain, which may be substituted with an amine group $NH_2$ or NHR (R=C1-C20 and especially C1-C6 alkyl, C3-C40 cycloalkyl or C6-C30 aromatic); or with a hydroxyl group, a thiol group, an aryl group (more particularly benzyl), which is substituted or unsubstituted; Z possibly being interrupted with a heteroatom (O, S or NH) or a carbonyl group (CO);
n represents an integer equal to 1 or 2.

Examples that may be mentioned include N-(3-acryloxy-2-hydroxypropyl)-3-aminopropyltriethoxysilane, 4-aminobutyltriethoxysilane, 3-aminopropylmethyl-diethoxysilane, 3-aminopropyltriethoxysilane, 3-aminopropyltris(methoxyethoxyethoxy)silane, bis(methyldiethoxysilylpropyl)amine, bis[3-(triethoxysilyl)propyl]urea, 3-(2,4-dinitrophenylamino)propyltriethoxysilane, hydroxymethyltriethoxysilane, mercaptomethylmethyldiethoxysilane, 3-mercaptopropyltriethoxysilane, o-(methacryloxyethyl)-N-(triethoxysilylpropyl)urethane, N-(3-methacryloxy-2-hydroxypropyl)-3-aminopropyltriethoxysilane, o-(propargyloxy)-N-(triethoxysilylpropyl)urethane, (3-triethoxysilyl-propyl)-t-butylcarbamate, triethoxysilylpropylethylcarbamate, N-(3-triethoxysilylpropyl)gluconamide, N-(3-triethoxysilylpropyl)-4-hydroxybutyramide, 3-(triethoxysilylpropyl)-p-nitrobenzamide, N-(triethoxysilylpropyl)-O-polyethylene oxide urethane, ureidopropyltriethoxysilane and o-(vinyloxyethyl)-N-(triethoxysilylpropyl)urethane, and mixtures thereof.

The silane may serve to promote the attachment of the copolymer to the keratin support.

The silane, alone or as a mixture, may be present in a proportion of from 0.5% to 30% by weight, especially 1% to 25% by weight or even 2% to 20% by weight, relative to the weight of the composition.

An agent for hydrolysis of said silane, especially an acidic agent such as lactic acid, citric acid, pyruvic acid, malic acid, hydrochloric acid or sulfuric acid, or mixtures thereof, may also be added to the composition, in combination with the silane.

The hydrolysis agent, alone or as a mixture, may be present in a proportion of from 0.01% to 20% by weight, especially 0.5% to 10% by weight or even 1% to 5% by weight, relative to the weight of the composition, so as to obtain a pH preferably of about 10.

This hydrolysis agent is especially added so as to start the phase of hydrolysis of the copolymer, which will allow its introduction in its hydrolyzed form, i.e. in the form of oligomers and not in its monomer form.

The compositions according to the invention may be in any galenical form conventionally used for topical application, and especially in the form of an aqueous, alcoholic or aqueous-alcoholic solution or suspension; an oily solution or suspension; a solution or dispersion of the lotion or serum type; an emulsion of liquid or semi-liquid consistency of the milk or cream type, obtained by dispersing a fatty phase in an aqueous phase (O/W) or, conversely, (W/O); an aqueous or anhydrous gel, an ointment, a loose or compact powder to be used in this form or to be incorporated into an excipient, or any other cosmetic form. These compositions may be packaged, especially in pump bottles or in aerosol containers, so as to apply the composition in vaporized form or in the form of a mousse. Such packaging forms are indicated, for example, when it is desired to obtain a spray or a mousse for treating the hair. The compositions in accordance with the invention may also be in the form of creams, gels, emulsions, lotions or waxes. When the composition according to the invention is packaged in the form of an aerosol in order to obtain a lacquer or a mousse, it comprises at least one propellant.

The compositions according to the invention comprise a cosmetically acceptable medium, i.e. a medium that is compatible with keratin materials, especially facial or bodily skin, the lips, the hair, the eyelashes, the eyebrows and the nails.

Depending on their nature and the intended use of the composition, the ingredients of the cosmetically acceptable medium may be present in usual amounts, which may be readily determined by a person skilled in the art, and which may be, for each ingredient, between 0.01% and 80% by weight.

Mention may especially be made of the following ingredients, alone or as a mixture: nonionic, cationic, anionic or amphoteric surfactants; hydrophilic solvents (alcohols) or hydrophobic solvents (alkanes); cationic, anionic or nonionic silicones bearing hydrophilic or hydrophobic grafts, which may or may not be phenylated; plasticizers, for example of polyol type; spreading agents or coalescers; liquid or solid fatty substances such as fatty alcohols, fatty acids, plant or mineral oils and plant or mineral waxes; conditioning agents such as cationic polymers including polyamines; polymers, especially styling polymers, which are in particular anionic (neutralized or non-neutralized), cationic or nonionic; pH agents (bases or acids); organic or mineral pigments or colorants; fillers such as nacres, $TiO_2$, resins and clays; sunscreens; fragrances; peptizers; preserving agents; amino acids; vitamins.

The cosmetic composition according to the invention may be in the form of a product for caring for, cleansing and/or making up bodily or facial skin, the lips, the eyebrows, the eyelashes, the nails and the hair, an antisun or self-tanning product, a body hygiene product, or a haircare product, especially for caring for, cleansing, styling, shaping or coloring the hair.

The composition especially finds a particularly advantageous use in the field of haircare, especially for holding the hairstyle or shaping the hair, or for the care, cosmetic treatment or cleansing of the hair. The haircare compositions are preferably shampoos, hair conditioners, styling or care gels, care lotions or creams, conditioners, hairsetting lotions, blow-drying lotions, hair styling and fixing compositions such as lacquers or sprays; hair restructuring lotions; lotions or gels for preventing hair loss, antiparasitic shampoos, antidandruff lotions or shampoos, and anti-seborrhoea treating shampoos. The lotions may be packaged in various forms, especially in vaporizers, in pump bottles or in aerosol containers so as to apply the composition in vaporized form or in the form of a mousse.

The composition may also be in the form of a hair coloring product, especially an oxidation dye or direct dye, optionally in the form of coloring shampoos; in the form of a permanent-waving, relaxing or bleaching composition, or alternatively in the form of a rinse-out composition, to be applied before or after dyeing, bleaching, permanent-waving or relaxing the hair, or alternatively between the two steps of a permanent-waving or relaxing operation.

The composition according to the invention may also be in the form of a care composition, especially a moisturizer, for bodily or facial skin, the lips and/or the integuments, especially a care product for cosmetically treating the skin and especially for moisturizing it, making it smooth, depigmenting it, nourishing it, protecting it against sunlight, or giving it a specific cosmetic treatment. Thus, it may be a lip-care base, a fixing base for lipsticks, an antisun or artificial tanning composition, a facial care composition (a day, night, anti-ageing or moisturizing composition); a matting composition; a skin cleansing composition, for example a makeup-removing product or a bath or shower gel, or a cleansing bar or soap; a body hygiene composition, especially a deodorant or anti-perspirant product, or alternatively a hair-removing composition or an aftershave gel or lotion. It may also be in the form of a makeup product for bodily or facial skin, the lips, the eyelashes, the nails or the hair; in particular a foundation, a blusher, a makeup rouge, an eye-shadow, a concealer product, an eyeliner, a mascara, a lipstick, a lip gloss, a lip pencil; a nail varnish, a nailcare product; a temporary tattoo product for bodily skin.

Even more particularly, the composition according to the invention finds an advantageous application in holding the hairstyle or shaping the hair, or alternatively in caring for, cosmetically treating or cleansing the hair.

One subject of the invention is thus a cosmetic treatment process, especially for making up, caring for, cleansing, coloring or shaping keratin materials, especially bodily or facial skin, the lips, the nails, the hair and/or the eyelashes, comprising the application to said materials of a cosmetic composition comprising at least one compound according to the invention.

Preferably, it is a cosmetic treatment process for conditioning the hair, in particular to give it or improve its suppleness, disentangling, smoothing, combability and manageability.

The application of the composition may optionally be followed by a heat treatment step.

The composition may also be in the form of a kit in two or more parts.

These parts may be intended for mixing together at the time of use or alternatively for application successively to the keratin substrate to be treated, in particular the hair. These successive application steps may or may not be interrupted by a step of manual drying, for example with a towel, or by means of an appliance, for instance a hairdryer.

In one preferred case of the invention, the composition comprising the dispersion according to the invention is used in leave-in mode.

In one preferred case of the invention, the composition comprising the dispersion according to the invention is used in combination with a heating appliance for shaping the hair, such as a curling iron, a waving iron, a crimping iron, a straightening iron or heated curlers. The temperature of the heating appliance used is preferably between 60° C. and 200° C.

In one preferred embodiment, the composition according to the invention may be applied to wet or dry hair, a step optionally followed by partial or total drying of the hair, optionally followed by the application of a heating tool, which may be a hair-dryer or a tool for simultaneously applying a mechanical constraint and heating (straightening iron, waving iron, crimping iron or curling iron, using or not using steam). The temperature of the tool is preferably between 60° C. and 200° C.

The invention is illustrated in greater detail in the examples that follow.

EXAMPLE 1

A/Preparation of the Dispersions 10 g of polysiloxane/polyurea copolymer (Belsil UD-80) are dissolved in an organic phase formed from 30 g of ethyl acetate, 0.5 g of cyclopentadimethylsiloxane (D5) and 10 g of hexanol. This mixture is added with stirring (magnetic bar) to 130 g of an aqueous 0.1% sodium lauryl ether sulfate solution. This dispersion is then homogenized by stirring with an Ultra-Turrax blender at 13 000 rpm for 15 minutes.

An opaque white dispersion is thus obtained, from which the hexanol and ethyl acetate are evaporated off under vacuum on a rotary evaporator.

An aqueous dispersion (1) of polysiloxane/polyurea copolymer comprising 8.9% of copolymer and also 0.45% of D5 and 0.17% of surfactant, is finally obtained.

Dispersions (2) to (10) below, in which the surfactant and the copolymer are identical to those of dispersion (1), are prepared in an identical manner.

|  |  | Copolymer | Organic phase | Surfactant | Water |
|---|---|---|---|---|---|
| Dispersion (1) | Before evaporation | 10 g | 30 g ethyl acetate + 0.5 g of D5 | Hexanol: 10 g | 0.19 g | 130 g |
|  | After evaporation | 8.9% | D5: 0.45% | Hexanol: 0% | 0.17% | 90.5% |
| Dispersion (2) | Before evaporation | 7.5 g | D6: 82.5 g | Hexanol: 7.5 g | 1.7 g | 300 g |
|  | After evaporation | 3% | D6: 33% | Hexanol: 0% | 0.7% | 63.3% |
| Dispersion (3) | Before evaporation | 7.5 g | D6: 82.5 g | Hexanol: 7.5 g | 1.7 g | 300 g |
|  | After evaporation | 5.7% | D6: 62.7% | Hexanol: 0% | 1.3% | 30.3% |
| Dispersion (4) | Before evaporation | 30 g | D6: 330 g | Hexanol: 30 g | 6.94 g | 1172 g |
|  | After evaporation | 5.8% | D6: 63.8% | Hexanol: 0% | 1.3% | 29.1% |
| Dispersion (5) | Before evaporation | 30 g | Isododecane: 330 g | Hexanol: 30 g | 6.9 g | 1172 g |
|  | After evaporation | 4.9% | Isododecane: 53.9% | Hexanol: 0% | 1.1% | 40.1% |

-continued

|  |  | Copolymer | Organic phase | Surfactant | Water |
|---|---|---|---|---|---|
| Dispersion (6) | Before evaporation | 3.75 g | — | Hexanol: 33.75 g | 0.87 g | 296 g |
|  | After evaporation | 7.4% | — | Hexanol: 0% | 1.7% | 90.9% |
| Dispersion (7) | Before evaporation | 3.75 g | Isododecane: 3.75 g | Hexanol: 33.75 g | 0.87 g | 296 g |
|  | After evaporation | 5.9% | Isododecane: 5.9% | Hexanol: 0% | 1.4% | 86.8% |
| Dispersion (8) | Before evaporation | 20 g | — | Hexanol: 180 g | 4.6 g | 693 g |
|  | After evaporation | 20.8% | — | Hexanol: 0% | 4.8% | 74.4% |
| Dispersion (9) | Before evaporation | 20 g | Isododecane: 60 g | Hexanol: 137 g | 4.6 g | 1013 g |
|  | After evaporation | 9.9% | Isododecane: 29.7% | Hexanol: 0% | 2.3% | 58.1% |
| Dispersion (10) | Before evaporation | 20 g | Cetiol UT: 60 g | Hexanol: 137 g | 4.6 g | 1013 g |
|  | After evaporation | 9.9% | Cetiol UT: 29.7% | Hexanol: 0% | 2.3% | 58.1% |

D6: cyclohexadimethylsiloxane

Cetiol UT: undecane/tridecane from Cognis.

B/Application in Two Stages After Pretreatment of the Hair with a Silane

Dispersions (1) and (3)-(10) are diluted in distilled water so as to have a final copolymer concentration of 3.75% by weight. Dispersion (2) is used undiluted.

They are applied to the hair, after pretreatment of the hair with the following formulation: aminopropyltriethoxysilane (10% active material) in a thickened aqueous solution (0.3% hydroxyethylcellulose) adjusted to pH 10 with lactic acid. The pretreatment is performed with 1 g of formulation for 2.7 g of hair. There is no leave-on time, and, after application, the hair is dried with a hairdryer.

Under these conditions, the remanence of formulations (1) to (10) increases from 4 shampoo washes to 6 shampoo washes, while at the same time conserving the cosmetic qualities of fineness and feel.

|  | Disentangling | Powdering/particles |
|---|---|---|
| Reference | 1 | 4 |
| Dispersion (4) | 5 | 0 |

EXAMPLE 2

A/Preparation of the Dispersions

The polysiloxane/polyurea copolymer (Belsil UD80) is dissolved in hexanol. This solution is added to an aqueous solution of cationic surfactant (cetyltrimethylammonium chloride) diluted in water and stirred with an Ultra-Turrax blender at 13 000 rpm. The mixture is homogenized for 30 minutes and the hexanol is then removed on a rotary evaporator. An opaque white aqueous dispersion is thus obtained, the composition of which is given below.

|  |  | Copolymer | Organic phase | Surfactant | Water |
|---|---|---|---|---|---|
| Dispersion (11) | Before evaporation | 20 g | 140 g Hexanol | 4.8 g | 1964 g |
|  | After evaporation | 15.6% | 0% | 3.7% | 80.7% |
| Dispersion (12) | Before evaporation | 20 g | 140 g Hexanol | 4.8 g | 1964 g |
|  | After evaporation | 8.5% | 0% | 2.0% | 89.5% |
| Dispersion (13) | Before evaporation | 40 g | 280 g Hexanol | 9.6 g | 3928 g |
|  | After evaporation | 6.9% | 0% | 1.6% | 91.5% |

2/Addition of Amino Silane

An aqueous solution of aminopropyltriethoxysilane (APTES) is prepared, comprising:

| APTES | 50% by weight |
|---|---|
| lactic acid | qs pH 10 |
| deionized water | qs 100% |

The aqueous solution of APTES is added, with stirring, to the dispersion prepared above, and the dilution is adjusted with deionized water.

The following formulations are finally obtained (weight %):

|  | Formulation 1 | Formulation 2 | Formulation 3 |
|---|---|---|---|
| Dispersion (11) | 24% | — | — |
| Dispersion (12) | — | 44.1% | — |
| Dispersion (13) | — | — | 54.4% |
| 50% APTES solution | 20% | 20% | 20% |
| Deionized water | qs 100% | qs 100% | qs 100% |

3/Demonstration of the Effect on the Shaping of the Hair 1 g of formulation is applied to a lock of 2.7 g of natural hair. After drying, shaping is performed using a heating tool such as a curling iron, applied for 30 seconds, with the thermostat set for a temperature of between 140 and 180° C. After cooling, the lock is suspended in ambient medium. The shape setting and its hold over time are evaluated, at T0 and after 6 shampoo washes.

The resistance of the coating to shampooing is evaluated in the following manner: 1 g of Ultra Doux shampoo from Garnier is deposited on the prewetted lock; the lock is massaged from the root to the end in 10 passes; the lock is then rinsed in water for 10 seconds. The operation is repeated six times in a row. After drying, the iron is reapplied and the lock is again suspended for evaluation of the shape.

In the comparative formulation, the 50% APTES solution is replaced with deionized water.

It is noted that the addition of amino silane in dispersions (11) to (13) gives a tighter shape, which holds better over time; this effect is also more remanent after six shampoo washes.

The invention claimed is:

1. A composition, comprising:
(i) an aqueous dispersion of a non-ionic polysiloxane/polyurea copolymer obtained from a reaction between:
a) a polymer of the formula:

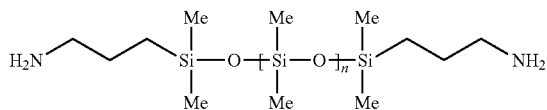

wherein the value of n is such that an average molecular weight of the polymer is between 300 and 10,000 g/mol; and
b) at least one diisocyanate of formula (II): OCN—R—NCO, wherein R is a linear, branched and/or cyclic, saturated or unsaturated, or aromatic, C 1-20 divalent alkylene group;
(ii) a silane selected from the group consisting of 4-aminobutyltriethoxysilane, 3-aminopropylmethyldiethoxysilane, 3-aminopropyltriethoxysilane, 3-aminopropyltris(methoxyethoxyethoxy)silane, and a mixture thereof; and
(iii) an agent for hydrolysis of the silane.

2. The composition according to claim 1, wherein a proportion of the hydrolysis agent is from 0.1% to 20% by weight, relative to the weight of the composition.

3. The composition according to claim 1, which is in the form of a product for caring for, cleansing and/or making up bodily or facial skin, the lips, the eyebrows, the eyelashes, the nails and the hair, an antisun or self-tanning product, a body hygiene product, or a haircare product.

4. The composition according to claim 1, wherein the agent for hydrolysis of the silane comprises at least one acid selected from the group consisting of lactic acid, citric acid, pyruvic acid, malic acid, hydrochloric acid and sulfuric acid.

5. The composition according to claim 1, wherein the silane is 3-aminopropyltriethoxysilane.

6. The composition according to claim 1, wherein the aqueous dispersion is obtained via a dispersion process comprising:
dissolving the non-ionic copolymer in an organic phase;
preparing an aqueous phase comprising one or more surfactants,
mixing together the organic and aqueous phases, and
then emulsifying the organic and aqueous phases.

7. The composition as claimed in claim 6, wherein the organic phase comprises a liquid compound (at 20-25° C., 1 atm.) that is insoluble in water and is solubilizing for the copolymer, wherein the liquid compound is
a linear or branched, saturated or unsaturated, optionally cyclic or aromatic C5-C30 alcohol or polyol, which may contain a heteroatom;
an ester of a monoalcohol or a polyol and of a monoacid or a polyacid, an ester of general formula R3-O—CO—R4, in which R3 and R4, which may be identical or different, are linear, branched, or cyclic, saturated or unsaturated, C3-C30 hydrocarbon-based radical;
a ketone of the formula R3-CO—R4 in which R3 and R4, which may be identical or different, are linear, branched, or cyclic, saturated or unsaturated, C3-C30 hydrocarbon-based radical;
an aromatic hydrocarbon;
a linear, cyclic or branched C5-C30 alkane;
a volatile or nonvolatile silicone oil.

8. The composition according to claim 6, wherein the surfactant is a cationic surfactant.

9. The composition according to claim 1, wherein the non-ionic polysiloxane/polyurea copolymer is present in an amount of 0.01% to 30% by weight of polymer solids relative to the weight of the cosmetic composition.

10. The composition according to claim 1, wherein the non-ionic polysiloxane/polyurea copolymer is present in an amount of 0.1% to 20% by weight of polymer solids relative to the weight of the cosmetic composition.

11. The composition according to claim 1, wherein the non-ionic polysiloxane/polyurea copolymer is present in an amount of 0.5% to 10% by weight weight of polymer solids relative to the weight of the cosmetic composition.

12. The composition according to claim 1, wherein the non-ionic polysiloxane/polyurea copolymer is present in an amount of 1% and 5% by weight of polymer solids relative to the weight of the cosmetic composition.

13. The composition according to claim 1, wherein the silane is added in an amount of from 0.5% to 30% by weight relative to the weight of the composition.

14. The composition according to claim 1, wherein the silane is added in an amount of from 1% to 25% by weight relative to the weight of the composition.

15. The composition according to claim 1, wherein the silane is added in an amount of from 2% to 20% by weight relative to the weight of the composition.

16. The composition according to claim 4, wherein the hydrolysis agent is present in a proportion of from 0.5% to 10% by weight relative to the weight of the composition.

17. The composition according to claim 16, wherein the hydrolysis agent is present in a proportion of from 1% to 5% by weight relative to the weight of the composition.

18. A kit in two or more parts, comprising at least one cosmetic composition according to claim 1.

19. A cosmetic treatment process, comprising applying a cosmetic composition according to claim 1 for making up, caring for, cleansing, coloring or shaping keratin materials.

* * * * *

UNITED STATES PATENT AND TRADEMARK OFFICE
CERTIFICATE OF CORRECTION

PATENT NO. : 8,877,167 B2
APPLICATION NO. : 13/146224
DATED : November 4, 2014
INVENTOR(S) : Xavier Schultze et al.

Page 1 of 1

It is certified that error appears in the above-identified patent and that said Letters Patent is hereby corrected as shown below:

Title Page, Item (75), "Xavier Schultze, Les Pavillos sous Bois" should read
--Xavier Schultze, Les pavillons sous Bois--;

Title Page, Item (87), "PCT Pub. Date: Aug. 5, 2011" should read
--PCT Pub. Date: Aug. 5, 2010--.

In the Claims,

Column 22, line 9, Claim 7, "20-25°C.," should read --20-25°C,--;
line 38, Claim 11, "weight weight" should read --weight--.

Signed and Sealed this
Thirty-first Day of March, 2015

Michelle K. Lee
*Director of the United States Patent and Trademark Office*